United States Patent
Klomp

[19]

[11] Patent Number: 6,152,993
[45] Date of Patent: Nov. 28, 2000

[54] METHOD FOR INHIBITING THE PLUGGING OF CONDUITS BY GAS HYDRATES

[75] Inventor: Ulfert C. Klomp, Amsterdam, Netherlands

[73] Assignee: Shell Oil Company, Houston, Tex.

[21] Appl. No.: 09/192,923

[22] Filed: Nov. 16, 1998

[51] Int. Cl.⁷ .................................................. C07C 9/00
[52] U.S. Cl. ................................................ 95/153; 585/15
[58] Field of Search ............................. 95/153; 96/235, 96/FOR 118; 585/15, 950

[56] References Cited

U.S. PATENT DOCUMENTS

| | | | |
|---|---|---|---|
| 3,213,593 | 10/1965 | Hendrix ................................... | 585/15 |
| 4,973,775 | 11/1990 | Sugier et al. ............................. | 585/15 |
| 5,331,105 | 7/1994 | Duncum et al. ......................... | 585/15 |
| 5,460,728 | 10/1995 | Klomp et al. ............................ | 585/15 |
| 5,491,269 | 2/1996 | Colle et al. .............................. | 585/15 |
| 5,583,273 | 12/1996 | Colle et al. .............................. | 585/15 |
| 5,639,925 | 6/1997 | Sloan, Jr. et al. ........................ | 585/15 |
| 5,648,575 | 7/1997 | Klomp et al. ............................ | 585/15 |
| 5,744,665 | 4/1998 | Costello et al. .......................... | 585/15 |
| 5,789,635 | 8/1998 | Durand et al. ............................ | 585/15 |
| 5,817,898 | 10/1998 | Delion et al. ............................. | 585/15 |
| 5,841,010 | 11/1998 | Rabeony et al. .......................... | 585/15 |
| 5,874,660 | 2/1999 | Colle et al. .............................. | 585/15 |
| 5,879,561 | 3/1999 | Klomp et al. ............................ | 585/15 |
| 5,981,816 | 11/1999 | Sinquin et al. ........................... | 585/15 |

FOREIGN PATENT DOCUMENTS

| | | |
|---|---|---|
| 93/25798 | 6/1993 | WIPO . |
| 96/341777 | 4/1996 | WIPO . |

*Primary Examiner*—Duane S. Smith

[57] ABSTRACT

A method is disclosed for inhibiting the plugging of a conduit for the transport of hydrocarbon fluids by gas hydrates, wherein use is made of a hydrate formation inhibitor component of formula $$(R_1)(R_2)(R_3)(R_4)A^+Y^- \qquad (I)$$

wherein two of $R_1$–$R_4$ are independently normal or branched alkyls having 4 or 5 carbon atoms, two of $R_1$–$R_4$ are independently representing organic moieties having at least 8 carbon atoms, A represents a nitrogen or a phosphorus atom, Y represents an anion and wherein at least one of $R_1$–$R_4$ represents a $-(CH_2-CHR_5-O)_p-(CH_2)_q-(CHR_6-CH_2)_r-(CH_2-CHR_7)_s-(CHR_8)_t-O-C(O)-R_9$ moiety with the meaning as defined in the description. Compositions containing a hydrate formation inhibitor component according to formula I and a hydrocarbon having from one to eight hydrocarbons as well as the hydrate formation inhibitor components, such as the di-esters of di-butyl-di-isopropanol (or -di-isobutanol) ammonium bromide and coconut fatty acid are believed to be novel.

24 Claims, 1 Drawing Sheet

METHOD FOR INHIBITING THE PLUGGING OF CONDUITS BY GAS HYDRATES

BACKGROUND OF THE INVENTION

This invention relates to a method and compound for inhibiting the plugging by gas hydrates of conduits containing a mixture of low-boiling hydrocarbons and water. In particular, it relates to a method and compound for continuing the flow of a mixture of hydrocarbons and water through a conduit after a shutdown which caused separation of hydrate crystals from the mixture.

The problem of the formation of gas hydrates (clathrates of gases in a lattice consisting of water molecules) is well known in the art. Low-boiling hydrocarbons, in particular methane, may under conditions of elevated pressure and reduced temperature tend to form gas hydrate crystals with water present in natural gas or crude oil.

Such gas hydrate crystals, when allowed to form and grow inside a conduit such as a pipeline, tend to block or even damage the conduit. A number of methods has been suggested to prevent such blocking of which the use of crystal growth inhibitors is considered to be very attractive.

In International Patent Application Publication WO 96/34177 the use of a class of hydrate formation inhibitors is described having the general formula $(R_1)(R_2)(R_3)(R_4)A^+Y^-$ wherein two of $R_1$–$R_4$ are independently normal or branched alkyls having 4 or 5 carbon atoms, two of $R_1$–$R_4$ are independently representing organic moieties having at least eight carbon atoms, A represents a nitrogen or a phosphorus atom and Y represents an anion.

Attractive results have been obtained when using the di-ester of di-butyl-di-ethanol ammonium bromide and coconut fatty acid, both with respect to decreasing the temperature at which hydrates tend to be formed (as described in experiment A 3b of said patent specification) and with respect to restarting the flow of the medium after stopping (as described in experiment B 1b of said specification). In the experiment B 1b it is described that after a temperature decrease of 11° C., followed by stopping the circulation of the medium used which resulted in the slow separation of a layer of very fine hydrate crystals from the hydrate forming medium, the circulation could be restarted whereby the layer of loose powder hydrates became readily resuspended into the hydrocarbon liquids resulting in the formation of the hydrate suspension which was observed prior to shutdown.

One of the problems still to be solved in managing the flow of suspended gas hydrates in conduits is being able to restart the flow after an interruption, either scheduled or unscheduled, when powder hydrates have been formed under rather severe conditions. Even with the preferred di-ester of di-butyl-di-ethanol ammonium bromide and coconut fatty acid restarts at rather severe conditions appear to be problematic.

SUMMARY OF THE INVENTION

It has now surprisingly been found that a specific group of esters, in addition to having the attractive properties as described in WO 96/34177 also exhibits an improved restart performance when subjected to rather severe conditions which makes them very attractive for such duties.

The present invention thus relates to a method for inhibiting the plugging of a conduit, the conduit containing a mixture comprising an amount of hydrocarbons having from one to eight carbon atoms and an amount of water wherein the amounts of hydrocarbons and water could form hydrates at conduit temperatures and pressures, the method comprising the steps of:

adding to the mixture an amount of a hydrate formation inhibitor component of formula $$(R_1)(R_2)(R_3)(R_4)A^+Y^- \qquad (I)$$

wherein two of $R_1$–$R_4$ are independently normal or branched alkyls having 4 or 5 carbon atoms, two of $R_1$–$R_4$ are independently representing organic moieties having at least 8 carbon atoms, A represents a nitrogen or phosphorus atom, Y represents an anion and wherein at least one of $R_1$–$R_4$ represents a
—$(CH_2$—$CHR_5$—$O)_p$—$(CH_2)_q$—$(CHR_6$—$CH_2)_r$—$(CH_2$—$CHR_7)_s$—$(CHR_8)_t$—$O$—$C(O)$—$R_9$ moiety wherein $R_5$–$R_8$ each independently represent a hydrogen atom or a $C_1$–$C_4$ alkyl group and at least one of $R_6$–$R_8$ is not a hydrogen atom; p represents 0 or an integer of up to 50; q, r, s and t are 0, 1 or 2 and together at least 1 and not more than 4 and wherein when q represents 1 or 2 the sum of r, s and t is at least 1 and, wherein when t and the sum of q, r, s and t represent 2, $R_8$ does not represent a methyl group; and $R_9$ represents an (cyclo)alkyl, alkenyl, aryl, arylalkyl, arylalkenyl, alkylaryl or alkenylaryl group having at least a carbon chain of 6 atoms, the amount of hydrate formation inhibitor component being effective to inhibit formation of hydrates in the mixture at conduit temperatures and pressures, and flowing the mixture containing the hydrate formation inhibitor component through the conduit.

Preferably, A represents nitrogen and two of $R_1$–$R_4$ independently contain between 8 and 20 carbon atoms, preferably in the range from 10 to 16 carbon atoms.

DETAILED DESCRIPTION OF THE INVENTION

Suitably, compounds are used wherein two of $R_1$–$R_4$ contain the same number of carbon atoms, each being at least 8. Preferably, use can be made of components wherein two of $R_1$–$R_4$ represent cocoyl moieties (i.e. the alkyl chain present in coconut fatty acids or similar compounds). Preference is given to compounds wherein $R_6$, $R_7$ and $R_8$ independently represent hydrogen or a methyl or ethyl group.

Preferred ammonium compounds in accordance with the present invention are those wherein p is zero, the sum of q, r and s is 2 and $R_9$ represents an alkyl or alkenyl group of between 9 and 18 carbon atoms. Very good results have been obtained with compounds for which q and t are 1 and $R_8$ represents a methyl or ethyl group.

Suitably, the anion ($Y^-$) represents a hydroxide, a carboxylate, a halide such as chloride or bromide, a sulphate or an organic sulphonate. Preferably, $Y^-$ represents a chloride, bromide or sulphate.

The presence of the carboxylic moiety in the compounds in accordance with the invention is of great advantage because of their biodegradable properties which renders them eminently suitable for the envisaged use. A further advantage in the envisaged use is that such compounds are sparingly soluble in water which allows discarding production water containing only marginal concentrations of such compounds.

The amount of hydrate formation inhibitor compound to be used lies suitably between 0.05 and 11% wt, based on the water content of the hydrocarbon/water mixture. Preferably, the amount is between 0.1 and 5% wt, in particular between 0.1 and 0.5% wt, based on the water content as defined.

If desired, corrosion inhibitors may be added to the hydrocarbon/water mixture. Corrosion inhibitors known to those skilled in the art can be suitably applied. If desired, polymers of ethylenically unsaturated N-heterocyclic carbonyl compounds can be added to the hydrocarbon/water mixture. Reference is made to the polymers or copolymers of N-vinyl-2-pyrrolidone as described in International Patent Application Publication WO 93/25798.

Compounds according to formula I, in which two of $R_1$–$R_4$ are independently representing organic moieties having at least 8 carbon atoms, A represents a nitrogen or a phosphorus atom, Y represents an anion, and wherein at least one of $R_1$–$R_4$ represents a —$(CH_2$—$CHR_5$—$O)_p$—$(CH_2)_q$—$(CHR_6$—$CH_2)_r$—$(CH_2$—$CHR_7)_s$—$(CHR_8)_t$—$O$—$C(O)$—$R_9$ moiety wherein $R_5$–$R_8$ each independently represent a hydrogen atom or a $C_1$–$C_4$ alkyl group and at least one of $R_6$–$R_8$ is not a hydrogen atom; p represents 0 or an integer of up to 50; q, r, s and t are 0, 1 or 2 and together at least 1 and not more than 4 and wherein when q represents 1 or 2 the sum of r, s and t is at least 1 and, wherein when t and the sum of q, r, s and t represent 2, $R_8$ does not represent a methyl group; and $R_9$ represents an (cyclo)alkyl, alkenyl, aryl, arylalkyl, arylalkenyl, alkylaryl or alkenylaryl group having at least a carbon chain of 6 atoms, are believed to be novel.

Suitable compounds are those in which A represents nitrogen and two of $R_1$–$R_4$ independently contain between 8 and 20 carbon atoms, preferably in the range from 10 to 16 carbon atoms. Further suitable compounds are those in which two of $R_1$–$R_4$ contain the same number of carbon atoms, each being at least 8.

Preference is given to compounds in which two of $R_1$–$R_4$ represents cocoyl moieties (i.e. the alkyl chain present in coconut fatty acids or similar compounds). In particular, preference is given to compounds in which $R_6$, $R_7$ and $R_8$ independently represent hydrogen, a methyl group or an ethyl group.

Preferred ammonium compounds are those in which p is zero, the sum of q, r, s and t is 2 and $R_9$ represents an alkyl or alkenyl group of between 9 and 18 carbon atoms; in particular compounds in which q and t are 1 and $R_8$ represents a methyl or ethyl group whilst r and s are zero.

Suitably, the anion ($Y^-$) represents a hydroxide, a carboxylate, a halide (such as chloride or bromide), a sulphate or an organic sulphonate. Preferably, $Y^-$ represents a chloride, bromide or sulphate.

Most preferred compounds are the di-ester of di-butyl di-isopropanol ammonium bromide and coconut fatty acid and the di-ester of di-butyl di-isobutanol ammonium bromide and coconut fatty acid.

DESCRIPTION OF EQUIPMENT

Figure 1:
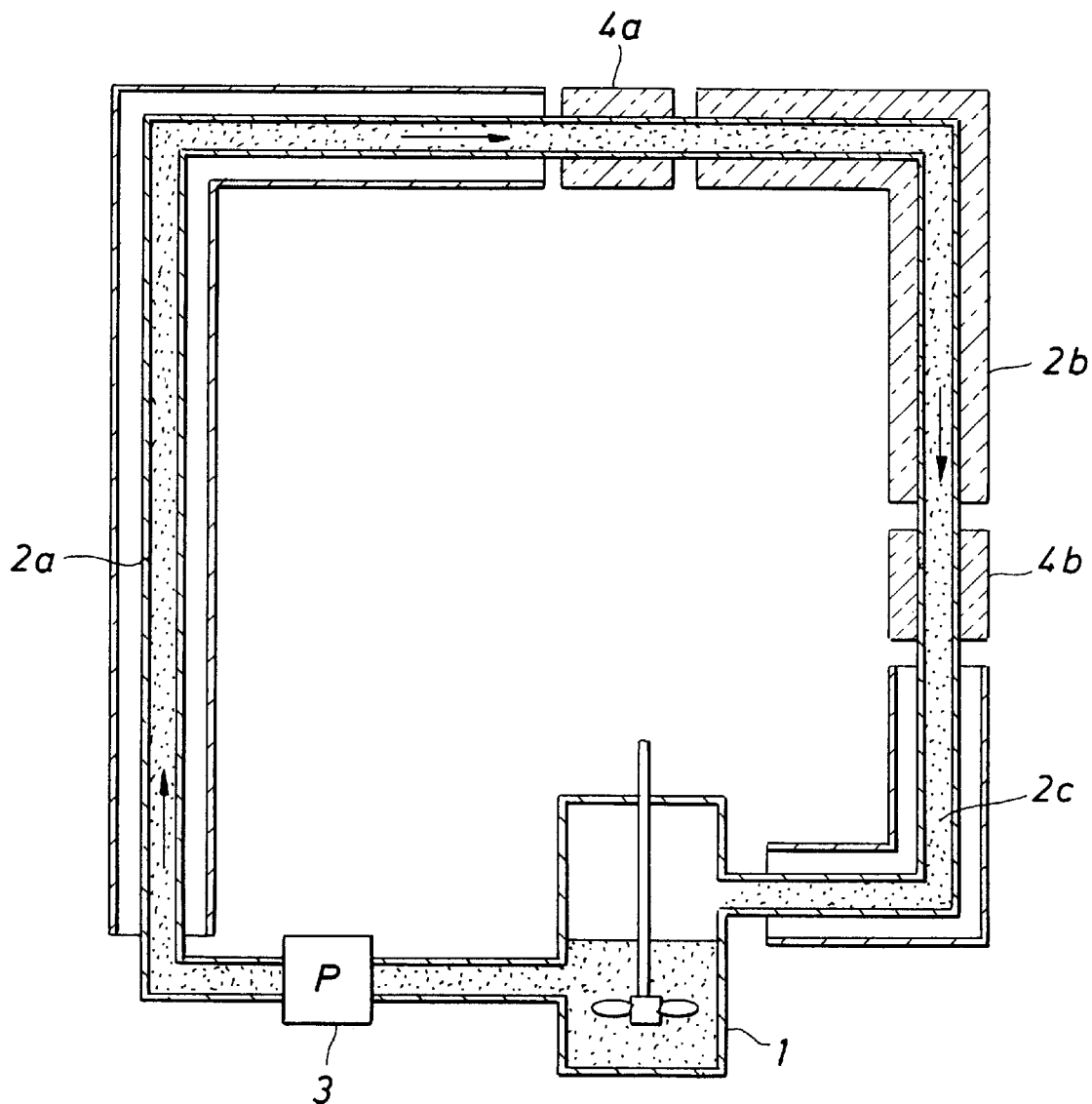
FIG. 1 and the following Example will illustrate the invention.

In the experiments that are detailed below field conditions were simulated by using a high-pressure flow loop facility which is schematically shown in FIG. 1 and which consists of a stainless steel pipeloop (2a–c) having an inner diameter of 19 mm and an effective length of 108 meters, a mixing tank (1) and a gear pump (3) for circulating a hydrate forming mixture of water and liquid hydrocarbons through the loop. The pipeloop can be seen as being divided into 9 sections (each having a length of 12 meters) and each of which is equipped with a thermometer and a differential pressure meter allowing the monitoring of the pressure drop over each individual section.

Sections 1–6 (2a) and section 9 (2c) are surrounded by a coaxial pipe through which a temperature-controlled liquid is circulated in counter-flow to the hydrate forming medium (which flows from section 1 to section 9).

Sections 7 and 8 (2b) are thermally well insulated and equipped with viewing windows (mounted near the inlet of section 7 (4a) and the outlet of section 8 (4b) to allow the visual observation of the hydrate forming medium in the pipeloop.

Hydrate formation is triggered by cooling 1 cm$^2$ of the inner surface of the pipeloop near the end of section 3 to a constant temperature of $-15°$ C. This "cold spot" was switched-off immediately after the first hydrates were formed.

Standard Filling and Pre-Conditioning Procedure

In all experiments described hereafter, the loop facility (having a total volume of 62.5 liters) was (at a temperature of 24° C.) initially filled with 5 liters of water, 39.2 liters of a hydrocarbon liquid, such as SHELLSOL D60 (trade name for a mixture of paraffinic and naphthenic hydrocarbons, mainly in the $C_{10}$–$C_{12}$ range, available from Shell Oil Company, Houston, Tex.) and 3.2 kilograms of propane. Subsequently, methane was introduced until the equilibrium pressure was 78 bara. This procedure leads to the formation of a three-phase system (i.e. a vapour phase, a liquid aqueous phase and a liquid hydrocarbon phase) in which can form stable hydrates at temperatures below 19° C. In all experiments the liquid phases of the hydrate forming medium were circulated through the pipe loop at a rate of 120 grams/second (or 540 liters per hour) which corresponds to a Reynolds number of approximately 8000 (turbulent flow). Prior to the start of each experiment the hydrate forming medium was circulated for approximately one day at a temperature of 23° C. to obtain thermodynamic equilibrium and an even distribution of the liquid phases throughout the entire system.

The effect of an additive (hydrate forming inhibitor component) was assessed by comparing the experimental results of a blank test (in which no additive had been added to the hydrate forming medium) with those of an additive test (in which the system was doped with the additive concerned) and which test was carried out under the same conditions of the blank test.

The experiments represent the hydrate recirculation mode in which the temperature of the hydrate forming medium is kept constant throughout the entire test facility.

Preparation of active compounds:

I. Preparation of the di-cocoyl ester of di-butyl di-isopropanol ammonium bromide:

a) Preparation of di-butyl amino-propanol-2

In a vessel 516 g dibutylamine (ex Aldrich) and 296 g butanol (ex Merck) were mixed and heated under nitrogen to 100° C. The pressure was 1 bar. About 100 g propylene oxide was added causing the pressure to rise to 2 bar. A further amount of 132 g propylene oxide was added causing the pressure to rise to about 3 bar.

Thereafter the total mixture was heated to 120° C. This caused the pressure to rise to 5 bar which dropped to 3.3 bar after 90 minutes. The reaction mixture was kept overnight and then subjected to flash distillation at reducing pressure. This yielded 498 g of (dibutyl-amino) propanol-2 (purity >95%).

b) Preparation of dibutyl di-2-hydroxypropyl ammonium bromide 234 g of the product obtained under a) was mixed with 468 g water, 234 g isopropanol and 169 g hydrogen bromide (48% wt) and heated under nitrogen to 70° C. 58 g propylene oxide was added in the course of a few minutes, causing an increase in the pressure from 1.64 bar to 2.03 bar. After 2 hours the pressure had become constant at 1.85 bar.

The crude product was worked up by flashing off the solvent followed by 2× desalting in isopropanol. Non-polar organics were removed by dissolving the sample in water, raising the pH to 14 and extracting the water layer twice with diethylether. After readjustment of the pH with hydrogen bromide the solution was subjected to evaporation to dryness. A polar organic impurity, propylene glycol, was removed by slurrying with diethylether. The final amount of propylene glycol in the otherwise pure product (yield 145 g) amounted to less than 3% mole.

c) Preparation of the dicocoylester of dibutyl di-isopropanol ammonium bromide

Product (48.8 g) obtained under b) and 164 g cocoyl anhydride were stirred in Rotavap equipment at 100° C. The ammonium salt is solid, does not melt and does not dissolve under the prevailing conditions. After stirring for 2 hours at 100° C. a nearly homogeneous mixture had been formed. According to $^1$H-NMR a complete conversion had taken place.

By means of wiped film evaporation (120° C./4.10$^{-2}$ mbar) 147 g of crude quaternary ammonium compound were obtained. Since the crude compound still contained some higher molecular weight carboxylic acids and anhydrides (preventing crystallisation of the ammonium compound from common solvents) it was subjected to a treatment with acetic anhydride (stirring for 1 hour at ambient temperature). After filtration of some precipitate, the liquid product was concentrated at 50° C./3.10$^{-2}$ mbar using Rotavap equipment. After subjecting it to a further purification step by means of wiped film evaporation (100° C. at 3.10$^{-2}$ mbar) the quaternary ammonium compound was obtained in 75% purity as characterised by $^1$H-NMR and $^{13}$C-NMR, the remainder consisting of anhydrides. Precipitation from 3 liters of pentane yielded 50 g of the pure dicocoyl ester of di-2-hydroxypropyl ammonium bromide.

$^{13}$C-NMR data: 13 ppm:2C; 14 ppm:2C; 19 ppm:2C; 20 ppm:2C; 22 ppm:2C; 24 ppm:2+2C; 29 ppm:ca 14C; 32 ppm:2C; 34 ppm:2C; 62 ppm:2C; 63 ppm:2C; 65 ppm:2C and 172 ppm:2C.

$^1$H-NMR: 0.9 ppm:CH$_3$ (ex coco), 6H; 1.0 ppm:CH$_3$ (ex butyl), 6H; 1.2–2.1 ppm:div. CH$_2$, ca 46H; 2.3 ppm:CH$_2$CO, 4H; 3.2–3.4 ppm:C$_3$H$_7$CH$_2$N, 4H; 3.6–4.0 and 4.2–4.4 ppm:NCH$_2$CH(CH$_3$)O, 4H; 5.3–5.5 ppm:CHOCO, 2H.

When a sample of the compound produced was subjected to saponification under standard conditions it was found that the acids present in the product were the same as initially present in the starting cocoyl compounds.

II. Preparation of the dicocoyl ester of dibutyl di-isobutanol ammonium bromide.

a) Preparation of di-butyl amino-butanol-2

In a 1.7 liter Medinex autoclave were mixed 310 g of di-butyl amine (ex Aldrich), 134 g butanol and 125 g butylene oxide (ex Aldrich). The autoclave was flushed 4 times with 5 bar nitrogen. The mixture is heated to 120° C. and kept under stirring for 16 hours at this temperature. After cooling down the contents of the autoclave are subjected to distillation using a Vigreux column. The product fraction (analysed using Gas Chromatography) amounted to 306 g (yield: 88%).

b) Preparation of di-butyl-di-2-butanol ammonium bromide

In a 1.7 liter Medinex autoclave were mixed 251 g of product obtained under a), 400 g of water, 300 g of isopropanol, 83 g butylene oxide (ex Aldrich) and 169 g hydrogen bromide (48% wt). The autoclave was flushed 4 times with 5 bar nitrogen. The mixture is heated to 80° C. and kept under stirring for 48 hours at this temperature. After cooling down the contents of the autoclave, 0.5 liters of isopropanol/water is removed using Rotavap equipment. Sodium hydroxide is added to obtain pH 14. After addition of 500 ml water, the product is extracted twice with 300 ml diethylether to remove amines present. The aqueous layer is then acidified using hydrogen bromide until pH 1–2. Thereafter water is removed by distillation (80° C./vacuum). Still remaining water is removed using azeotropic distillation with toluene.

The residue is stirred in isopropanol and filtrated to remove inorganic salts. The residue is then subjected to evaporation to dryness (yielding about 150 g). By stirring the product with 500 ml diethylether, the viscous liquid mixture slowly transforms into a crystalline solid in diethylether. After filtration, the solid is stirred with 500 ml diethylether, filtrated again and dried under high vacuum. The diethylether fraction contained 24 g butanediol.

The solid is then stirred in 300 ml of CH$_2$Cl$_2$ and filtrated again to remove the last remnants of inorganic salts. By concentrating the filtrate a viscous oil is obtained. After a final treatment with 500 ml diethylether, the solid reappeared and was subjected to filtration and drying. The yield was 116 g (29%) and the structure confirmed with both $^1$H-NMR and $^{13}$C-NMR.

c) Preparation of the dicocoylester of di-butyl di-isobutanol ammonium bromide

Coco anhydride (150 g) and di-butyl di-2-butanol ammonium bromide obtained in step b) (50 g) were mixed in Rotavap equipment and heated to 100° C. At that temperature the product from step b) has melted causing a two layer system. After continuous stirring for one hour a homogeneous mixture had been formed. A sample was subjected to $^1$H-NMR analysis and showed nearly quantitative conversion.

The product obtained was subjected three times to wiped film evaporation (120° C./10$^{-1}$ mbar, then at 120° C./5.10$^{-2}$ mbar and finally at 120° C./3.10$^{-2}$ mbar). The residue weighs 134 g and contains some acid, anhydride and ammonium compound.

Finally, the product was stirred for 1 hour with acetic acid anhydride at ambient temperature. A solid product is formed which is separated by filtration and is identified as long chain anhydride. The acetic acid anhydride and acetic acid are removed by Rotavap distillation (50° C. and 2 mbar). The product is subjected to wiped film evaporation at 120° C. and 4.10$^{-2}$ mbar. The yield of the isobutanol compound amounts to 119 g (70% purity).

Experiment 1a (Blank Test)

The test facility was filled with 5 liters of water, 3.2. kilograms of propane and 39.2 liters of a mixture consisting of 85% SHELLSOL D 60 and 15% of SHELLSOL R (SHELLSOL is a trademark), after which methane was added until the equilibrium pressure at 24° C. was 78 bar. This procedure leads to the formation of a three-phase system (i.e. a vapour phase, a liquid aqueous phase and a liquid hydrocarbon phase) in which can form stable hydrates at temperatures below 19° C. The liquid phases of the hydrate forming medium were circulated through the pipeloop at a rate of 120 g/second (or 540 liters/hour) which corresponds to a Reynolds number of approximately 8000 (turbulent flow). Prior to the start of each experiment the hydrate forming medium was circulated for approximately one day at a temperature of 23° C. to obtain thermodynamic equilibrium and an even distribution of the liquid phases throughout the entire system.

The experiment was started by cooling the hydrate forming medium at rate of 1° C./hr. Because no heating was applied in the ninth section, the temperature of the hydrate forming medium was independent of the position of the medium in the test facility. In this type of test the hydrates which are carried by the flow become severely crushed when they pass through the gear pump. During this experiment the first increase in the pressure drop was observed after four hours by which time the temperature of the medium was 18.8° C. The circulation could be maintained for another hour during which the pressure drop increased continuously until the loop became completely blocked by hydrates. At the time of blocking the temperature of the hydrate forming medium was 18.0° C.

Experiment 1b

This experiment was identical to experiment 1a except for the addition of 12.5 grams of the diester of dibutyl-diethanol ammonium bromide and coconut fatty acid, giving a concentration of 0.25% wt of hydrate formation inhibitor component. Eleven hours after the start of the cooling cycle, at which the temperature of the medium was 12° C., the circulating liquids became hazy whereas the pressure in the system dropped rapidly indicating that a substantial amount of hydrates were formed. The cooling cycle was continued for another 11 hours after which the temperature of the hydrate forming mixture was reduced to 1° C. and only a slight increase of the pressure drop over the loop was observed. The medium was circulated for another two hours during which the pressure drop did not increase. At this stage the pressure of the system had dropped to 52 bar indicating that practically all water was converted into hydrates. Subsequently the circulation was stopped resulting in the slow separation of a layer of very fine hydrate crystals from the hydrate forming medium. This shut-down condition was maintained for the next 22 hours during which the temperature of the medium was kept at 1° C. When the circulation was restarted the layer of loose powder hydrates became readily resuspended into the hydrocarbon liquids resulting in the formation of the hydrate suspension which was observed prior to shut-down. Also the pressure drop over the pipeloop had not increased with respect to the situation before the circulation was stopped.

Experiment 1c

The experiment as described in experiment 1b was repeated except for allowing a drop in temperature of 14° C. Restart of the circulation, which was smoothly possible under the conditions as described in experiment 1b, after 2.5 hours of shut down was not possible. When performing a similar test with a drop in temperature of 18° C., a restart was hardly possible even after 1 hour after shut down.

Experiment 1d (According to the Invention)

The experiment as described in experiment 1b was repeated except for using 0.50% wt of the diester of dibutyl diisopropanol ammonium bromide and coconut fatty acid as the hydrate formation inhibitor component. When allowing a temperature drop of 14° C. the circulation could be restarted without any problem, even after a shutdown of 16.8 hours. When the experiment was repeated allowing a temperature drop of 18° C. a smooth restart could be effected even after 20.3 hours.

Experiment 1e

The experiment as described in experiment 1b was repeated except for using 0.50% wt of the diester of dibutyl dipropanol ammonium bromide and coconut fatty acid. When allowing a temperature drop of 14° C. a restart, even after 0.5 hours after shut-down failed completely.

Experiment 1f (According to the Invention)

The experiment as described in experiment 1b was repeated except for using 0.5% wt of the diester of dibutyl diisobutanol ammonium bromide and coconut fatty acid. When allowing a temperature drop of 18° C. a smooth restart could be achieved even after a shut-down of no less than 17 hours.

From the experimental data it will be clear that the branched components used in the process according to the invention have a marked and unexpected performance advantage with respect to restart of circulation after a shut-down under severe conditions.

What is claimed is:

1. A method for inhibiting the plugging of a conduit, the conduit containing a mixture comprising an amount of hydrocarbons having from one to eight carbon atoms and an amount of water wherein the amounts of hydrocarbons and water could form hydrates at conduit temperatures and pressures, the method comprising the steps of:

adding to the mixture an amount of a hydrate formation inhibitor component of formula $$(R_1)(R_2)(R_3)(R_4)A^+Y^- \qquad (I)$$

wherein two of $R_1$–$R_4$ are independently
normal or branched alkyls having 4 or 5 carbon atoms,
two of $R_1$–$R_4$ are independently representing organic moieties having at least 8 carbon atoms,
A represents a nitrogen or phosphorus atom,
Y represents an anion
and wherein at least one of $R_1$–$R_4$ represents a
—(CH$_2$—CHR$_5$—O)$_p$—(CH$_2$)$_q$—(CHR$_6$—CH$_2$)$_r$—(CH$_2$—CHR$_7$)$_s$—(CHR$_8$)$_t$—O—C(O)—R$_9$ moiety wherein $R_5$–$R_8$ each independently represent a hydrogen atom or a $C_1$–$C_4$ alkyl group and at least one of $R_6$–$R_8$ is not a hydrogen atom; p represents 0 or an integer of up to 50; q, r, s, and t are 0, 1 or 2 and together at least 1 and not more than 4 and wherein when q represents 1 or 2 the sum of r, s, and t is at least 1 and, wherein when t and the sum of q, r, s and t represent 2, $R_8$ does not represent a methyl group; and $R_9$ represents an (cyclo)alkyl, alkenyl, aryl, arylalkyl, arylalkenyl, alkylaryl or alkenylaryl group having at least a carbon chain of 6 atoms,
the amount of hydrate formation inhibitor component being effective to inhibit formation of hydrates in the mixture at conduit temperatures and pressures, and
flowing the mixture containing the hydrate formation inhibitor component through the conduit.

2. The method according to claim 1, wherein A represents nitrogen and two of $R_1$–$R_4$ independently contain between 8 and 20 carbon atoms.

3. The method according to claim 1, wherein two of $R_1$–$R_4$ contain the same number of carbon atoms, each being at least 8.

4. The method according to claim 1, wherein $R_6$, $R_7$ and $R_8$ each independently represent hydrogen or a methyl or ethyl group.

5. The method according to claim 1, wherein p is zero, the sum of q, r, s, and t is 2 and $R_9$ represents an alkyl or alkenyl group of between 9 and 18 carbon atoms.

6. The method according to claim 1, wherein q and t are 1 and $R_8$ represents a methyl or ethyl group.

7. The method according to claim 1, wherein $R_9$ represents the carbon chain of coconut fatty acid or tallow fatty acid.

8. The method according to claim 1, wherein the anion represents a hydroxide, a carboxylate, a halide, a sulphate or an organic sulphonate.

9. The method according to claim 1, wherein between 0.05 and 11% wt, based on the water content, of the hydrate formation inhibitor component is added to the water/hydrocarbon mixture.

10. The method according to claim 1, wherein the amount of hydrate formation inhibitor component added is between 0.1 and 5% wt, based on the water content.

11. The method according to claim 1 wherein a corrosion inhibitor is added to the hydrocarbon/water mixture.

12. The method according to claim 1, wherein a polymer of an ethylenically unsaturated N-heterocyclic carbonyl compound is added to the hydrocarbon/water mixture.

13. The method according to claim 1, wherein the step of flowing the mixture containing the hydrate formation inhibitor component through the conduit is effected after a shutdown which caused separation of hydrate crystals from the mixture.

14. The method according to claim 1, wherein the step of flowing the mixture is effected with a hydrocarbon/water mixture which has been subjected during shutdown to a decrease in temperature of more than 12° C.

15. The method of claim 3 wherein $R_6$, $R_7$, and $R_8$ each independently represent hydrogen or methyl or ethyl group.

16. The method of claim 15 wherein p is zero, the sum of q, r, s and t is 2 and $R_9$ represents an alkyl or alkenyl group of between 9 and 18 carbon atoms.

17. The method of claim 3 wherein q and t are 1 and $R_8$ represents a methyl or ethyl group.

18. The method of claim 3 wherein $R_9$ represents the carbon chain of coconut fatty acid or tallow fatty acid.

19. The method of claim 3 wherein the anion represents a hydroxide, a carboxylate, a halide, a sulphate or an organic sulphonate.

20. The method of claim 3 wherein between 0.05 and 11% wt, based on the water content, of the hydrate formation inhibitor component is added to the water/hydrocarbon mixture.

21. The method of claim 3 wherein a corrosion inhibitor is added to the hydrocarbon/water mixture.

22. The method of claim 3 wherein a polymer of an ethylenically unsaturated N-heterocyclic carbonyl compound is added to the hydrocarbon/water mixture.

23. The method of claim 3 wherein the step of flowing the mixture containing the hydrate formation inhibitor component through the conduit is effected after a shutdown which caused separation of hydrate crystals from the mixture.

24. The method of claim 23 wherein the step of flowing the mixture is effected with a hydrocarbon/water mixture which has been subjected during shutdown to a decrease in temperature of more than 12° C.

* * * * *